(12) United States Patent
Kohut et al.

(10) Patent No.: US 7,651,991 B2
(45) Date of Patent: Jan. 26, 2010

(54) CLEANSING GEL

(75) Inventors: Michaela Kohut, Hamburg (DE);
Albrecht Doerschner, Hamburg (DE);
Magalie Racine, Hamburg (DE);
Stephan Ruppert, Hamburg (DE)

(73) Assignee: Beiersdorf AG, Hamburg (DE)

( * ) Notice: Subject to any disclaimer, the term of this patent is extended or adjusted under 35 U.S.C. 154(b) by 504 days.

(21) Appl. No.: 11/179,491

(22) Filed: Jul. 13, 2005

(65) Prior Publication Data
US 2006/0014662 A1    Jan. 19, 2006

(30) Foreign Application Priority Data
Jul. 14, 2004    (DE)    ........................ 10 2004 034 915

(51) Int. Cl.
*A61K 7/50*    (2006.01)
(52) U.S. Cl. ........................ 510/156; 510/424; 510/426; 510/428; 510/490; 510/499
(58) Field of Classification Search ........................ None
See application file for complete search history.

(56) References Cited

U.S. PATENT DOCUMENTS

| | | | |
|---|---|---|---|
| 5,776,872 A * | 7/1998 | Giret et al. ................... | 510/124 |
| 5,980,877 A | 11/1999 | Baravetto et al. | |
| 6,165,479 A | 12/2000 | Wheeler | |
| 6,174,522 B1 | 1/2001 | Baravetto et al. | |
| 6,267,978 B1 * | 7/2001 | Sang et al. ................... | 424/401 |
| 6,410,593 B1 | 6/2002 | De Mesanstourne et al. | |
| 6,451,333 B1 * | 9/2002 | Beerse et al. ................ | 424/405 |
| 6,528,070 B1 * | 3/2003 | Bratescu et al. ............. | 424/401 |
| 6,533,873 B1 | 3/2003 | Margosiak et al. | |
| 6,635,702 B1 | 10/2003 | Schmucker-Castner et al. | |
| 6,682,725 B1 | 1/2004 | Dieing et al. | |
| 2003/0103926 A1 | 6/2003 | Maubru | |
| 2003/0103927 A1 | 6/2003 | Maubru | |
| 2003/0103929 A1 | 6/2003 | Maubru | |
| 2003/0108503 A1 | 6/2003 | Maubru et al. | |
| 2003/0108578 A1 | 6/2003 | Maubru | |
| 2004/0001796 A9 | 1/2004 | Maubru | |
| 2004/0087668 A1 | 5/2004 | Schmucker-Castner et al. | |
| 2004/0265261 A1 | 12/2004 | Kohut et al. | |
| 2004/0267170 A1 | 12/2004 | Liste et al. | |
| 2005/0048856 A1 | 3/2005 | Hauser et al. | |
| 2005/0158268 A1 | 7/2005 | Schmucker-Castner et al. | |

FOREIGN PATENT DOCUMENTS

| | | | |
|---|---|---|---|
| DE | 19731764 | | 1/1999 |
| EP | 0947192 | | 10/1999 |
| EP | 1275371 | | 1/2003 |
| EP | 1291000 | | 3/2003 |
| EP | 1291001 | | 3/2003 |
| EP | 1291002 | | 3/2003 |
| EP | 1291003 | | 3/2003 |
| EP | 1291005 | | 3/2003 |
| EP | 1470813 | | 10/2004 |
| WO | 97/32559 | | 9/1997 |
| WO | 98/18443 | | 5/1998 |
| WO | WO 99/09952 | * | 3/1999 |
| WO | 01/19946 | | 3/2001 |
| WO | 01/76552 | | 10/2001 |
| WO | 03/030807 | | 4/2003 |
| WO | 03/097005 | | 11/2003 |
| WO | 2004/006882 | | 1/2004 |

* cited by examiner

*Primary Examiner*—Necholus Ogden, Jr.
(74) *Attorney, Agent, or Firm*—Greenblum & Bernstein, P.L.C.

(57) ABSTRACT

A cosmetic cleansing gel comprising myreth sulfate, cocamidopropyl betaine, a cross-linked acrylate copolymer and water. The gel has a viscosity of from about 1,500 to about 10,000 mPa·s. This Abstract is not intended to define the invention disclosed in the specification, nor intended to limit the scope of the invention in any way.

30 Claims, No Drawings

CLEANSING GEL

CROSS-REFERENCE TO RELATED APPLICATIONS

The present application claims priority under 35 U.S.C. §119 of German Patent Application No. 10 2004 034 915.0, filed Jul. 14, 2004, the entire disclosure whereof is expressly incorporated by reference herein.

BACKGROUND OF THE INVENTION

1. Field of the Invention

The present invention relates to a cosmetic cleansing gel which comprises myreth sulfate, cocamidopropyl betaine, cross-linked acrylate copolymer and water.

2. Discussion of Background Information

The desire for clean skin probably is as old as mankind because dirt, sweat and residues of dead skin are ideal media for the growth of all kinds of pathogens and parasites. The joy in body hygiene was continuously increased when it became possible in the 1960's to formulate, in addition to "classic" soaps, liquid cleansing agents with newly developed synthetic surfactants. Since then, bathing and showering have become an integral part of our daily life. Today consumers can choose from a large variety of products for cleansing the different parts of the body.

A special group of skin cleansing products are the facial cleansing products. Since facial skin is particularly sensitive, products which are especially mild and non-irritant to skin are employed for cleansing facial skin. In most cases, gels, i.e., semi-solid, more or less transparent systems are used for this purpose.

Cleansing gels contain water, surfactants and thickeners (gelling agents) as main constituents.

The surfactants are the detersive substances in the cleansing gels. Due to their specific molecule structure with both hydrophilic (water attracting) and hydrophobic (water repellent) groupings in the same molecule they are capable of reducing the surface tension of water, thereby facilitating the removal of dirt. Depending on their charge, the surfactants are classified as anionic, cationic, non-ionic and amphoteric. Due to their capability of reducing the surface tension of water, surfactants bring about a foaming of the preparation.

The thickeners, also called gel formers, form a three-dimensional network in the cleansing gel, in which network the liquid (usually water) is immobilized. Apart from salts, polymers such as polyacrylates are most frequently employed as thickeners. These polymers are added to the preparation to be thickened at a neutral pH, and subsequently they are deprotonated by the addition of base, thereby transforming the preparation into a viscous gel.

Basically, cleansing gels should be both mild and soft to the skin, and should form a sufficient amount of a creamy foam with fine pores. Further, the gels should be as transparent and clear as possible, because thereby it is possible to effectively incorporate therein optical effect materials, and because consumers prefer transparent preparations for esthetic reasons.

Conventional cleansing gels prepared according to the prior art show a number of shortcomings:

In order for the preparation to be mild and to not degrease the skin too much, only selected surfactants in low concentrations can be incorporated into the preparations. Such preparations are, however, not capable of producing sufficient foam. The foam produced is not particularly creamy and does not have fine pores, and collapses within a short period. Also, the viscosity of preparations with a low surfactant concentration cannot be increased in conventional manner by adding salts thereto.

To increase the viscosity of preparations with a low surfactant concentration, polymeric thickeners (e.g., carbopols) have to be added to the preparations. However, such thickeners interfere with the foaming of the preparations.

Usually, the combination of conventional surfactants and polymeric thickeners results in a turbid preparation. Optical effects such as, e.g., the addition of abrasives or glitter substances, are only insufficiently noticeable.

It would be desirable to overcome the shortcomings of the cleansing gels of the prior art and to provide mild cleansing gels with high foaming power and high transparency.

SUMMARY OF THE INVENTION

The present invention provides a cosmetic cleansing gel which comprises, based on the total weight of the gel,
(a) from about 1% to about 5% by weight of myreth sulfate;
(b) from about 1.5% to about 7% by weight of cocamidopropyl betaine;
(c) from about 2% to about 10% by weight of at least one cross-linked acrylate copolymer; and
(d) from about 70% to about 95% by weight of water.

The weight ratio (a):(b) is from about 0.1:1 to about 1.3:1 and the gel has a viscosity of from about 1,500 to about 10,000 mPa·s.

In one aspect, the gel may have a transmission at a wavelength of 420 nm of from about 50% to about 100%.

In another aspect, the gel may comprise one or more of the following: at least about 1.5% by weight of (a) and/or not more than about 3% by weight of (a); at least about 2% by weight of (b) and/or not more than about 5% by weight of (b); at least about 3% by weight of (c) and/or not more than about 7% by weight of (c).

In yet another aspect of the gel of the present invention, the weight ratio (a):(b) may be about 0.5:1.

In a still further aspect, the gel may further comprise from about 0.1% to about 2% by weight of one or more preservatives and/or from about 0.1% to about 2% by weight of one or more complex formers and/or from about 0.5% to about 10% by weight of one or more skin moisturizers and/or it may comprise one or more dyes.

In another aspect, the gel may further comprise an abrasive, a glitter substance, gas bubbles, an effect material, a color striation, oil droplets and/or emulsion droplets.

In yet another aspect, component (a) may comprise or consist of sodium myreth sulfate and/or the acrylate copolymer of component (c) may comprise a copolymer of at least one unsaturated carboxylic acid having from about 3 to about 10 carbon atoms.

The present invention also comprises a cosmetic cleansing gel which comprises, based on the total weight of the gel,
(a) from about 1.5% to about 3% by weight of myreth sulfate;
(b) from about 2% to about 5% by weight of cocamidopropyl betaine;
(c) from about 3% to about 7% by weight of at least one cross-linked acrylate copolymer; and
(d) from about 70% to about 93.5% by weight of water.

The weight ratio (a):(b) is from about 0.2:1 to about 1:1 and the gel has a viscosity of from about 1,500 to about 10,000 mPa·s.

In one aspect, the above gel may further comprise one or more of (i) from about 0.1% to about 2% by weight of one or more preservatives, (ii) from about 0.1% to about 2% by weight of one or more complex formers, and (iii) from about 0.5% to about 10% by weight of one or more skin moisturizers. For example, the gel may further comprise from about 0.2% to about 1.2% by weight of one or more preservatives and/or from about 0.2% to about 1% by weight of one or more complex formers and/or from about 2% to about 6% by weight of one or more skin moisturizers.

In another aspect of the gel, the weight ratio (a):(b) may be about 0.5:1.

In yet another aspect, the gel may comprise sodium myreth sulfate.

The present invention also provides a cosmetic cleansing gel which comprises, based on the total weight of the gel,
 (a) from about 1.5% to about 3% by weight of sodium myreth sulfate;
 (b) from about 2% to about 5% by weight of cocamidopropyl betaine;
 (c) from about 3% to about 7% by weight of at least one cross-linked acrylate copolymer;
 (d) from about 70% to about 93.5% by weight of water;

The weight ratio (a):(b) in the gel is from about 0.3:1 to about 0.8:1 and the gel has a viscosity of from about 1,500 to about 10,000 mPa·s.

In one aspect, the above gel may further comprise from about 0.2% to about 1.2% by weight of one or more preservatives, from about 0.2% to about 1% by weight of one or more complex formers, and from about 2% to about 6% by weight of one or more skin moisturizers.

The present invention also provides a container, e.g., a packaging receptacle, which comprises one of the above gels, including the various aspects thereof.

In one aspect, the container may be substantially transparent. In another aspect, the container may comprise a tube, a pump dispenser, or a bottle.

The present invention also provides a carrier which is impregnated with one of the above gels, including the various aspects thereof. In one aspect, the carrier may comprise a cloth and/or a pad.

The viscosity of the gel according to the present invention may be determined with a Haake Viskotester VT 02 (temperature 25° C.; spindle: rotating body 1 (diameter 24 mm); rotor speed: 62.5 $min^{-1}$).

Cleansing gels containing cross-linked acrylate copolymers are known per se. See, for example, WO 01/076552, WO 01/019946, EP 1291000, EP 1291001, EP1291002, EP1291003 und EP 1291005. However, these documents could not render obvious the present invention.

It is preferred according to the present invention for the concentration of myreth sulfate in the cleansing gel to be from about 1.5% to about 3% by weight, based on the total weight of the preparation.

Myreth sulfates which are preferred include in particular, the compounds Texapon K 14 S Spezial (Cognis), CASR-No. 68891-38-4, Standapol ES 40 (Cognis), CASR-No. 68585-34-2 and Zetesol 470 (Zschimmer&Schwarz), CAS-No. 25446-80-4.

According to the present invention it is preferred for the concentration of cocamidopropyl betaine in the cleansing gel to be from about 2% to about 5% by weight, based on the total weight of the preparation.

According to the present invention, cocamidopropyl betaine is the INCI designation for cocamidopropyl dimethylglycine, which has the CAS-No. 61789-40-0 (I).

Preferably, the weight ratio of myreth sulfate and cocamidopropyl betaine is about 0.5:1.

Preferred according to the present invention is the use of a compound which is sold by Noveon under the designation Carbopol Aqua SF-1. This compound is a slightly cross-linked, alkali-swellable acrylate copolymer which comprises three structural units, i.e., one or more carboxylic acid monomers having 3 to 10 carbon atoms, one or more vinyl monomers and, as third component, one or more mono- or polyunsaturated monomers.

It is preferred according to the present invention for the cross-linked acrylate copolymer to be incorporated into the cleansing gel in a concentration of from about 3% to about 7% by weight, based on the total weight of the preparation.

The light transmission according to the present invention may be measured with an Agilent 8453 Diode Array Spectrometer at a layer thickness of 1 cm. The measurement may be carried out at room temperature in the range of from 190 nm to 1,100 nm in intervals of 1 nm and with an integration time of 0.5 seconds. According to the present invention, the light transmission of the gel at a wavelength of 420 nm preferably is from about 50% to about 100%.

It is also advantageous for the cleansing gel according to the present invention to have a pH value of from about 6 to about 8.

Advantageous embodiments of the present invention include those which comprise one or more preservatives in a concentration of from about 0.1% to about 2% by weight, preferably from about 0.2% to about 1.2% by weight, based on the total weight of the preparation.

Examples of advantageous preservatives for use in the present invention include formaldehyde donors (such as, e.g., hydantoin which is commercially available, for example, under the trade name Glydant™ from Lonza), iodopropynyl butylcarbamate (commercially available, for example, from Lonza under the trade names Glycacil-L and Glycacil-S, and from Jan Dekker under the designation Dekaben LMB), parabens (i.e., alkyl p-hydroxybenzoates such as methyl, ethyl, propyl and/or butyl paraben), phenoxyethanol, ethanol, benzoic acid, and the like. Usually and according to the present invention, the preservation system preferably also comprises preservation aids such as, e.g., octoxyglycerin, glycine soja, etc. The above list of advantageous preservatives is not meant to be limiting. Rather, all preservatives which are approved for cosmetics or foodstuffs may be used to advantage for the purposes of the present invention.

Examples of particularly preferred preservatives according to the present invention are the parabens and phenoxyethanol.

Advantageous for the purposes of the present invention also is the presence in the cleansing gel of one or more complex formers in a total concentration of from about 0.1% to about 2% by weight, preferably from about 0.2% to about 1% by weight, based on the total weight of the preparation.

The complex former(s) may advantageously be selected from the usual compounds. Preferred examples thereof include tartaric acid and anions thereof, citric acid and anions thereof, and aminopolycarboxylic acids and anions thereof (e.g., ethylenediamine tetraacetic acid (EDTA) and anions thereof, nitrilotriacetic acid (NTA) and anions thereof, hydroxyethylenediaminotriacetic acid (HOEDTA) and anions thereof, diethyleneaminopentaacetic acid (DPTA) and anions thereof, trans-1,2-diaminocyclohexane tetraacetic acid (CDTA) and anions thereof.

Hydroxyethylenediaminotriacetic acid and, in particular, the sodium salt thereof ($Na_3HEDTA$), are particularly preferred examples of complex formers for use in the gel of the present invention.

According to the present invention it further is advantageous for the cleansing gel to comprise one or more skin moisturizers in a concentration of from about 0.5% to about 10% by weight, preferably from about 2% to about 6% by weight, based on the total weight of the preparation.

Examples of advantageous moisturizers include glycerin, lactic acid and/or lactates, in particular, sodium lactate, butylene glycol, propylene glycol, Biosaccaride Gum-1, Glycine Soja, Ethylhexyloxyglycerin, pyrrolidone carboxylic acid and urea. It further is advantageous to use polymeric moisturizers from the group of water-soluble and/or water-swellable polysaccharides and/or polysaccharides which can be gelled with the aid of water. Particularly, advantageous are, for example, hyaluronic acid, chitosan and/or a fucose-rich polysaccharide with the Chemical Abstracts No. 178463-23-5 which is commercially available, for example, under the designation Fucogel®1000 from SOLABIA S.A.

Particularly preferred according to the present invention is the use of glycerin as skin moisturizer.

It may further be advantageous for the cleansing gel according to the present invention to contain abrasives (e.g., peeling particles of polyethylene), glitter substances, effect materials, color striations, gas bubbles (in particular, air bubbles), pearlescent pigments, glimmer, oil droplets and/or emulsion droplets.

The cleansing gel of the present invention further may advantageously contain one or more dyes. Examples of suitable dyes include the known, water-soluble dyes which are approved for use in cosmetics.

Further cosmetic auxiliaries, active agents and additives may advantageously be added to the cleansing gel of the present invention. The following list of corresponding substances is in no way limiting and exhaustive, and represents but a small fraction of the substances which can be used in the gel of the present invention.

The aqueous phase of the cleansing gel of the present invention may advantageously include conventional cosmetic auxiliaries such as, e.g., alcohols, in particular, those of low carbon number, preferably ethanol and/or isopropanol, diols or polyols of low carbon number as well as ethers thereof, preferably propylene glycol, glycerin, butylene glycol, ethylene glycol, ethylene glycol monoethyl and monobutyl ethers, propylene glycol monomethyl, monoethyl and monobutyl ethers, diethyleneglycol monomethyl and monoethyl ethers and analogous products, polymers, foam stabilizers, electrolytes, pearlescence agents, anti-dandruff agents, plant extracts, vitamins, active agents.

Particularly advantageous preparations include those which comprise antioxidants as additives or active ingredients.

Non-limiting examples of further advantageous active ingredients for the purposes of the present invention include natural active agents and/or derivatives thereof such as, e.g., alpha-lipoic acid, phytoen, D-biotin, Coenzyme Q10, alpha-glucosylrutin, carnitine, carnosine, natural and/or synthetic isoflavonoids, creatine, creatinine, taurine and/or β-alanine, as well as 8-hexadecene-1, 16-dicarboxylic acid (dioic acid, CAS No. 20701-68-2; provisional INCI designation octadecendioic acid), licochalcone A, ascorbic acid and derivatives thereof, vitamin E and derivatives thereof, vitamin A and derivatives thereof, γ-oryzanol, panthenol and/or niacinamide.

A further active ingredient which is advantageous for the purposes of the present invention is polidocanol.

The amount of active ingredients (one or more compounds) in the preparation according to the present invention preferably is from about 0.001% to about 30% by weight, more preferably from about 0.05% to about 20% by weight, in particular, from about 0.1% to about 10% by weight, based on the total weight of the preparation.

In accordance with the present invention it is preferred for the preparation of the present invention to be stored in a tube, a pump dispenser or a bottle and to be dispensed from one of these receptacles. According to the invention, such receptacles are preferably substantially transparent.

Accordingly, tubes, pump dispensers or bottles which contain a preparation in accordance with the present invention are also an object of the present invention, with transparent receptacles being preferred.

It further is advantageous according to the present invention to apply the cleansing gel of the present invention to a carrier material (e.g., a cloth, a pad, a cotton pad, etc.). Corresponding carriers preferably comprise viscose, cotton and/or polyester fibers.

Accordingly, a carrier material (e.g., a cloth, a pad, a cotton pad, etc.) that is impregnated with a cleansing gel of this invention is also in accordance with the present invention, with the carrier material being preferably composed of viscose, cotton and/or polyester fibers.

DETAILED DESCRIPTION OF THE PRESENT INVENTION

The particulars shown herein are by way of non-limiting example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

Unless indicated otherwise, all amounts, proportions and percentages given in the following examples are by weight and are based on the total amount or weight of the preparations.

|  | Example No. | | | | |
| --- | --- | --- | --- | --- | --- |
|  | 1 | 2 | 3 | 4 | 5 |
| Sodium myreth sulfate | 5% | 4% | 3% | 3% | 3% |
| Cocoamidopropyl betaine | 7% | 5% | 4% | 2% | 1.5% |
| Laurylglucoside | — | 1% | — | 1% | 2% |
| Acrylates Copolymer | 4% | 5% | 4% | 3% | 7% |
| Sodium hydroxide | 0.5% | 0.5% | 0.5% | 0.5% | 0.5% |
| Glycerin | 5% | 10% | 2% | 10% | — |
| Polyquaternium-10 | 0.1% | — | 0.2% | — | 0.3% |
| Na$_3$HEDTA | 0.5% | 0.5% | 0.5% | 0.5% | 0.5% |
| Polyethylene | 1% | 1.5% | 2% | — | — |
| PEG-40 hydrogenated castor oil | — | 1% | 0.5% | 1% | — |
| Phenoxyethanol | 0.5% | 0.5% | 0.5% | 0.5% | 0.5% |
| Parabenes | 0.2% | 0.2% | 0.2% | 0.2% | 0.2% |
| Perfume | q.s. | q.s. | q.s. | q.s. | q.s. |
| Water | ad 100 | ad 100 | ad 100 | ad 100 | ad 100 |

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic cleansing gel, wherein the gel comprises, based on a total weight of the gel,
    (a) from about 1% to about 5% by weight of myreth sulfate;
    (b) from about 1.5% to about 7% by weight of cocamidopropyl betaine;
    (c) from about 2% to about 10% by weight of at least one cross-linked acrylate copolymer; and
    (d) from about 70% to about 95% by weight of water;
and wherein a weight ratio (a):(b) is from about 0.1:1 to about 1.3:1 and wherein the gel has a viscosity of from about 1,500 to about 10,000 mPa·s.

2. The gel of claim 1, wherein the gel has a transmission at a wavelength of 420 nm of from about 50% to about 100%.

3. The gel of claim 1, wherein the gel comprises at least about 1.5% by weight of (a).

4. The gel of claim 2, wherein the gel comprises not more than about 3% by weight of (a).

5. The gel of claim 1, wherein the gel comprises at least about 2% by weight of (b).

6. The gel of claim 5, wherein the gel comprises not more than about 5% by weight of (b).

7. The gel of claim 1, wherein the gel comprises at least about 3% by weight of (c).

8. The gel of claim 6, wherein the gel comprises not more than about 7% by weight of (c).

9. The gel of claim 1, wherein the weight ratio (a):(b) is about 0.5:1.

10. The gel of claim 1, wherein the gel further comprises from about 0.1% to about 2% by weight of one or more preservatives.

11. The gel of claim 1, wherein the gel further comprises from about 0.1% to about 2% by weight of one or more complex formers.

12. The gel of claim 1, wherein the gel further comprises from about 0.5% to about 10% by weight of one or more skin moisturizers.

13. The gel of claim 1, wherein the gel further comprises one or more dyes.

14. The gel of claim 1, wherein the gel further comprises at least one of an abrasive, a glitter substance, gas bubbles, a pearlescent pigment, glimmer, a color striation, oil droplets and emulsion droplets.

15. The gel of claim 1, wherein (a) comprises sodium myreth sulfate.

16. The gel of claim 1, wherein (a) consists of sodium myreth sulfate.

17. The gel of claim 1, wherein the acrylate copolymer comprises a copolymer of at least one unsaturated carboxylic acid having from about 3 to about 10 carbon atoms.

18. A cosmetic cleansing gel, wherein the gel comprises, based on a total weight of the gel,
    (a) from about 1.5% to about 3% by weight of myreth sulfate;
    (b) from about 2% to about 5% by weight of cocamidopropyl betaine;
    (c) from about 3% to about 7% by weight of at least one cross-linked acrylate copolymer; and
    (d) from about 70% to about 93.5% by weight of water;
and wherein a weight ratio (a):(b) is from about 0.2:1 to about 1:1 and wherein the gel has a viscosity of from about 1,500 to about 10,000 mPa·s.

19. The gel of claim 18, wherein the gel further comprises at least one of (i) from about 0.1% to about 2% by weight of one or more preservatives, (ii) from about 0.1% to about 2% by weight of one or more complex formers, and (iii) from about 0.5% to about 10% by weight of one or more skin moisturizers.

20. The gel of claim 19, wherein the gel further comprises at least one of (i) from about 0.2% to about 1.2% by weight of one or more preservatives, (ii) from about 0.2% to about 1% by weight of one or more complex formers, and (iii) from about 2% to about 6% by weight of one or more skin moisturizers.

21. The gel of claim 18, wherein the weight ratio (a):(b) is about 0.5:1.

22. The gel of claim 19, wherein (a) comprises sodium myreth sulfate.

23. A cosmetic cleansing gel, wherein the gel comprises, based on a total weight of the gel,
    (a) from about 1.5% to about 3% by weight of sodium myreth sulfate;
    (b) from about 2% to about 5% by weight of cocamidopropyl betaine;
    (c) from about 3% to about 7% by weight of at least one cross-linked acrylate copolymer;
    (d) from about 70% to about 93.5% by weight of water;
and wherein a weight ratio (a):(b) is from about 0.3:1 to about 0.8:1 and the gel has a viscosity of from about 1,500 to about 10,000 mPa·s.

24. The gel of claim 23, wherein the gel further comprises from about 0.2% to about 1.2% by weight of one or more preservatives, from about 0.2% to about 1% by weight of one or more complex formers, and from about 2% to about 6% by weight of one or more skin moisturizers.

25. The gel of claim 23, wherein the gel has a transmission at a wavelength of 420 nm of from about 50% to about 100%.

26. The gel of claim 25, wherein the gel is present in a transparent container.

27. The gel of claim 26, wherein the gel further comprises at least one of an abrasive, a glitter substance, gas bubbles, a pearlescent pigment, glimmer, and a color striation.

28. The gel of claim 26, wherein the container comprises at least one of a tube, a pump dispenser, and a bottle.

29. The gel of claim 1, wherein the gel is provided in combination with a carrier into which it is impregnated.

30. The gel of claim 29, wherein the carrier comprises at least one of a cloth and a pad.

* * * * *